(12) United States Patent
Heller et al.

(10) Patent No.: US 6,281,006 B1
(45) Date of Patent: *Aug. 28, 2001

(54) ELECTROCHEMICAL AFFINITY ASSAY

(75) Inventors: Adam Heller; Charles N. Campbell, both of Austin, TX (US)

(73) Assignee: Therasense, Inc., Alameda, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/138,888

(22) Filed: Aug. 24, 1998

(51) Int. Cl.⁷ .............................. C12M 1/40; C12M 1/34; G01N 27/327; G01N 27/26
(52) U.S. Cl. .............................. 435/287.9; 435/4; 435/6; 435/7; 435/7.1; 435/7.21; 435/7.97; 435/7.94; 435/14; 435/25; 435/26; 435/27; 435/28; 435/174; 435/176; 435/177; 435/180; 435/181; 435/188; 435/189; 435/190; 435/288; 435/291; 435/817; 436/806; 436/518; 436/531; 436/501; 204/153.12; 204/403; 204/418
(58) Field of Search .................. 435/28, 14, 7.5, 435/41, 7.1, 7.9, 176, 403, 5, 817, 288, 6, 91.2, 291, 7.93, 7.94, 962, 518, 25, 525; 436/501, 528, 531, 825, 533, 535, 806, 524; 204/403, 418, 291, 292, 153.12, 290, 415, 416; 422/82.01, 82.03; 205/777.5, 792; 525/333.3; 7/180, 181, 182, 4, 28

(56) References Cited

U.S. PATENT DOCUMENTS

| | | | |
|---|---|---|---|
| 4,840,893 | 6/1989 | Hill et al. | 435/6 |
| 4,945,045 | 7/1990 | Forrest et al. | |
| 5,089,112 * | 2/1992 | Skotheim et al. | 204/403 |
| 5,147,781 | 9/1992 | Rishpon et al. | 435/7.4 |
| 5,149,630 | 9/1992 | Forrest et al. | 435/7.9 |

(List continued on next page.)

FOREIGN PATENT DOCUMENTS

| | | |
|---|---|---|
| 2 276 724 | 10/1994 | (GB). |
| WO 90/05910 | 5/1990 | (WO). |
| WO 91/16630 | 10/1991 | (WO). |
| WO 97/27474 | 7/1997 | (WO). |
| WO 98/02743 | 1/1998 | (WO). |
| WO 98/35232 | 8/1998 | (WO). |

OTHER PUBLICATIONS

Garguilo et al. Analytical Chemica Acta, 1995, vol. 307/2–3, pp. 261–299.*

Allongue, P. et al., "Covalent Modification of Carbon Surfaces by Aryl Radicals Generated from the Electrochemical Reduction of Diazonium Salts", *J. Am. Chem. Soc*, vol. 119, No. 1, pp. 201–207 (Jan. 8, 1997).

Anderson, M., "Hybridization Strategy", *Gene Probes 2, A Practical Approach*, Hames and Higgins, eds., pp. 1–29 (1995).

Böni, J. et al., "Sensitive and Quantitative Detection of PCR–Amplified HIV–1 DNA Products by an Enzme Linked Immunoassay Following Solution Hybridization with Two Differently Labelled Oligonucleotide Probes", *Mol. Cell. Probes*, vol. 7, No. 5, pp. 361–371 (Oct. 1993).

Castillo, L. et al., "Analysis of Retinoic Acid Receptorβ Expression in Norman and Malignant Laryngeal Mucosa by a Sensitive and Routine Applicable Reverse Transcription–Polymerase Chain Reaction Enzyme–linked Immunosorbent Assay Method", *Clin. Cancer Res.*, vol. 3, No. 11, pp. 2137–2142 (Nov. 1997).

Chu, B., et al. "Derivatization of Unprotected Polynucleotides", *Nucleic Acids Res.*, vol. 11, No. 18, pp. 6513–6529 (1983).

(List continued on next page.)

*Primary Examiner*—Long V. Le
*Assistant Examiner*—Lisa V. Cook
(74) *Attorney, Agent, or Firm*—Merchant & Gould P.C.

(57) ABSTRACT

An electrochemical affinity assay system for detection of ligand—ligand receptor binding.

17 Claims, 8 Drawing Sheets

U.S. PATENT DOCUMENTS

| | | | |
|---|---|---|---|
| 5,198,367 | 3/1993 | Aizawa et el. | 435/518 |
| 5,262,035 * | 11/1993 | Gregg et al. | 204/403 |
| 5,264,104 | 11/1993 | Gregg et al. | 204/403 |
| 5,320,725 * | 6/1994 | Gregg et al. | 204/153.12 |
| 5,346,832 | 9/1994 | Aizawa et al. | 436/518 |
| 5,356,786 * | 10/1994 | Heller et al. | 435/14 |
| 5,391,272 * | 2/1995 | O'Daly et al. | 204/153.12 |
| 5,403,451 | 4/1995 | Riviello et al. | 204/153.1 |
| 5,534,132 * | 7/1996 | Vreeke et al. | 205/777.5 |
| 5,560,811 | 10/1996 | Briggs et al. | 204/451 |
| 5,589,136 | 12/1996 | Northrup et al. | 422/102 |
| 5,595,878 * | 1/1997 | Sood et al. | 435/6 |
| 5,665,222 * | 9/1997 | Heller et al. | 205/792 |
| 5,783,056 * | 7/1998 | Hampp et al. | 204/403 |
| 5,814,708 * | 9/1998 | Frechet et al. | 525/333.3 |
| 5,906,723 | 5/1999 | Mathies et al. | 204/603 |
| 5,922,183 * | 7/1999 | Rauh | 204/403 |
| 5,942,388 * | 8/1999 | Willner et al. | 435/6 |
| 5,968,745 * | 10/1999 | Thorp et al. | 435/6 |
| 5,972,199 * | 10/1999 | Heller et al. | 205/777.5 |
| 6,017,696 | 1/2000 | Heller | 435/6 |
| 6,045,676 | 4/2000 | Mathies et al. | 204/603 |
| 6,051,380 | 4/2000 | Sosnowski et al. | 435/6 |
| 6,060,327 | 5/2000 | Keen | 436/518 |
| 6,063,259 | 5/2000 | Wang et al. | 205/777.5 |
| 6,068,818 | 5/2000 | Ackley et al. | 422/50 |

OTHER PUBLICATIONS de Lumley–Woodyear, T. et al., "Polyacrylamide–Based Redox Polymer for Connecting Redox Centers of Enzymes to Electrodes", *Analytical Chemistry*, vol. 67, No. 8, pp. 1332–1338 (1995).

Dorenbaum, A. et al., "Transmission of HIV–1 in Infants Born to Seropositive Mothers: PCR–Amplified Proviral DNA Detected by Flow Cytometric Analysis of Immunoreactive Beads", *J. Acquired Immune Defic. Syndro.& Hum. Retrovirol.*, vol. 15, No. 1, pp. 35–42 (May 1, 1997).

Duan, C. et al., "Separation–Free Sandwich Enzyme Immunoassays Using Microporous Gold Electrodes and Self–Assembled Monolayer/Immobilized Capture Antibodies", *Anal. Chem.*, vol. 66, No. 9, pp. 1369–1377 (May 1, 1994).

Effenhauser, C. et al., "High–Speed Separation of Antisense Oligonucleotides on a Micromachined Capillary Electrophoresis Device", *Anal. Chem*, vol. 66, No. 18, pp. 2949–2953 (Sep. 15, 1994).

Green, N.M., "Avidin", *Advances in Protein Chemistry*, Anfinsen, Edsall and Richards, eds., vol. 29, pp. 85–133 (1975).

Gutiérrez, R. et al., "A Quantitative PCR–ELISA for the Rapid Enumeration of Bacteria in Refrigerated Raw Milk", *J. Appl. Microbiol.*, vol 83, No. 4, pp. 518–523 (Oct. 1997).

Hashimoto, K. et al., "Novel DNA Sensor for Electrochemical Gene Detection", *Analitica Chimica ACTA*, vol. 286, pp. 219–224 (1994).

Hashimoto, K. et al., "Sequence–Specific Gene Detection with a Gold Electrode Modified with DNA Probes and an Electrochemically Active Dye", *Anal. Chem.*, vol. 66, No. 21, pp. 3830–3833 (Nov. 1, 1994).

Horrocks, B. et al., "Scanning Electrochemical Microscopy. 24. Enzyme Ultramicroelectrodes for the Measurement of Hydrogen Peroxide at Surfaces", *Anal. Chem.*, vol. 65, No. 24, pp. 3605–3614 (Dec. 15, 1993).

Ivnitski, D. et al., "A One–Step, Separation–Free Amperometric Enzyme Immunosensor", *Biosens. & Bioelec.*, vol. 11, No. 4, pp. 409–417 (1996).

Kawagoe, J. et al., "Enzyme–Modified Organic Conducting Salt Microelectrode", *Anal. Chem.*, vol. 63, pp. 2961–2964 (Dec. 15, 1991).

Kopp, M. et al., "Chemical Amplification: Continuous–Flow PCR on a Chip", *Science*,vol. 280, pp. 1046–1048 (May 15, 1998).

Korri–Youssoufi, H. et al., "Toward Bioelectronics: Specific DNA Recognition Based on an Oligonucleotide–Functionalized Polypyrrole", *J. Am. Chem. Soc.*, vol. 119, No. 31, pp. 7388–7389 (Aug. 6, 1997).

Livache, T. et al., "Polypyrrole DNA Chip on a Silicon Device: Example of Hepatitis C Virus Genotyping", *Anal. Biochem.*, vol. 255, No. 2, pp. 188–194 (Jan. 15, 1998).

Meyerhoff, M. et al., "Novel Nonseparation Sandwich–Type Electrochemical Enzyme Immunoassay System for Detecting Marker Proteins in Undiluted Blood", *Clin. Chemistry*, vol. 41, No. 9, pp. 1378–1384 (1995).

Millan, K. et al., "Sequence–Selective Biosensor for DNA Based on Electroactive Hybridization Indicators", *Anal. Chem.*vol. 65, No. 17, pp. 2317–2323 (Sep. 1, 1993).

Millan, K. et al., "Voltammetric DNA Biosensor for Cystic Fibrosis Based on a Modified Carbon Paste Electrode", *Anal. Chem.*vol. 66, No. 18, pp. 2943–2948 (Sep. 15, 1994).

Napier, M et al., "Probing Biomolecule Recognition with Electron Transfer: Electrochemical Sensors for DNA Hybridization", *Bioconjugate Chem.*, vol. 8, No. 6, pp. 906–913 (Nov./Dec. 1997).

Nickerson, D. et al., "Automated DNA Diagnositics Using an ELISA–Based Oligonucleotide Ligation Assay", *Proc. Natl. Acad. Sci. U.S.A.*, vol. 87, No. 22, pp. 8923–8927 (Nov. 1990).

Ossewaarde, J.M. et al., "Detection of Amplified *Chlamydia trachomatis* DNA using a Microtiter Plate–Based Enzyme Immunoassay", *Eur. J. Clin. Microbiol. Infect. Dis.*, vol. 13, No. 9, pp. 732–740 (Sep. 1994).

Sakai, H. et al. "Local Detection of Photoelectrochemically Produced $H_2O_2$ with a "Wired" Horseradish Peroxidase Microsensor", *J. Phys. Chem.*, vol. 99, No. 31, pp. 11896–11900 (Aug. 3, 1995).

Singhal, P. et al., "Ultrasensitive Voltammetric Detection of Underivatized Oligonucleotides and DNA", *Anal. Chem.*, vol. 69, No. 23, pp. 4828–4832 (Dec. 1, 1997).

Takenaka, S. et al., "Electrochemically Active DNA Probes: Detection of Target DNA Sequences at Femtomole Level by High–Performance Liquid Chromatography with Electrochemical Detection", *Anal. Biochem.*, vol. 218, No. 2, pp. 436–443 (May 1, 1994).

Vreeke, M. et al., "Direct Electrical Detection of Dissolved Biotinylated Horseradish Peroxidase, Biotin, and Avidin", *Anal. Chem.*, vol. 67, No. 2, pp. 303–306 (Jan. 15, 1995).

Wiedemann, D. et al., "Strategies for Low Detection Limit Measurements with Cyclic Voltammetry", *Anal. Chem.*, vol. 63, pp. 2965–2970 (1991).

Xiao, L. et al., "Quantitation of RT–PCR Amplified Cytokine mRNA by Aequorin–Based Biolumminescence Immunoassay", *J. Immunol. Methods*, vol. 199, No. 2, pp. 139–147 (1996).

Xu, X–H et al., "Immobilization of DNA on an Aluminum(III) Alkanebisphosphonate Thin Film with Electrogenerated Chemiluminescent Detection", *J. Am. Chem. Soc.*, vol. 116, No. 18, pp. 8386–8387 (Sep. 7, 1994).

Xu, X–H et al., "Immobilization and Hybridization of DNA on an Aluminum(III) Alkanebisphosphonate Thin Film with Electrogenerated Chemiluminescent Detection", *J. Am. Chem. Soc.*, vol. 117, No. 9, pp. 2627–2631 (Mar. 8, 1995).

* cited by examiner

ELECTROCHEMICAL AFFINITY ASSAY

FIELD OF THE INVENTION

The invention relates to affinity assays for the detection of a biological ligand such as a protein, particularly an antibody, or a nucleic acid. In particular, the invention includes the efficient detection of bifunctional biological ligands, such an antibody in whole blood and in fluids of animals, plants and other organisms, or of DNA labeled with two or more biological ligands. More particularly, the invention relates to an affinity assay in which the binding of such a ligand to a ligand receptor results in an electrochemical signal, such as a current or a potential.

BACKGROUND OF THE INVENTION

Affinity assay systems are commonly used in clinical and non-clinical situations to detect, monitor, or confirm the identity, amount, or presence of a particular ligand. Examples include immunoassays for the detection of an antibody or antigen, such as enzyme linked immunoassay (ELISA) or radioimmunoassay (RIA). Such affinity assays confer specificity and sensitivity to the analysis of a particular ligand in a complex sample, such as blood or other body fluid.

Conventional affinity assays employing conventional labeling and detection techniques typically require washing and/or separation steps. In addition, many affinity assay systems require detection in a machine such as a spectrophotometer or fluorimeter. These are not practical when detection of the ligand in whole blood and other light absorbing or scattering biological fluids is desired. Some conventional affinity assays, not requiring such equipment, rely on visible color changes for detection of ligand, which is also not practical in an opaque or colored fluid such as blood. Furthermore, the commonly used detection compounds, of conventional assays, such as hydrogen peroxide, are rapidly eliminated by protective enzymes found in blood and other tissues, such as catalase.

An affinity assay providing sensitive, efficient, and rapid detection of a ligand in a complex sample medium, and particularly for detection in whole blood is needed. A preferred assay would not require washing or separation steps, sample removal to machinery for analysis, and most preferably, would utilize only materials contained or generated in its probe, materials available in the biological fluids analyzed or, if added, not rapidly decomposed by enzymes in biological fluids. An affinity assay satisfying these criteria would permit the production of affinity assay systems to detect ligands in whole blood. Such an affinity assay system is described in the instant invention.

SUMMARY OF THE INVENTION

The affinity assay system of the present invention is based on the electrical connection of the third member, upon its binding to the second member, when the second member is located on or in the redox polymer film on the detecting electrode. The connection of the detection marker to the electrode is via the conducting redox polymer. The affinity assay system of the invention is capable of detecting and/or quantitating a variety of specific ligands, including proteins and nucleic acids, without washing or separation steps. The affinity assay system of the invention operates in whole blood and in other unseparated biological fluids, such as those of tissues and living cell cultures, without added toxic or unstable agents.

The affinity assay system of the invention includes an electrode coated with a conducting redox polymer, preferably a redox hydrogel. The redox polymer has multiple fast redox centers. The system has at least three members. The first and second members and also the second and third members are capable of conjugating with each other, and therefore capable of binding with each other. The first member of the ligand—ligand receptor pair is immobilized within the redox polymer either through an affinity reaction or by covalent bonding. The second member of the ligand—ligand receptor pair binds to the first. The third member is labeled with an amplifying detection marker, such as a peroxidase. Generation of the detection compound, the substrate of the detection maker, is catalyzed by another enzyme, such as choline oxidase. The enzyme that catalyzes the generation of a detection compound is immobilized in the redox polymer, but its reaction centers are preferably not oxidized by oxidized redox centers of the polymer and are not reduced by reduced redox centers of the polymer when the electrode is poised at its operating potential.

In a preferred embodiment, the affinity assay system includes an electrode coated with an electron conducting redox polymer in which a strongly binding member of a bioconjugating couple, such as ss-DNA or ss-peptide DNA, avidin, or streptoavidin and a substrate generating enzyme, such as hydrogen peroxide-generating choline oxidase, are immobilized. ("ss" means single-stranded.) The first member of a ligand—ligand receptor pair is biotinylated or labeled with DNA or peptide DNA, and bound to the redox polymer via DNA hybridization or avidin-biotin coupling. The second member is bound then to the first. The third member is labeled with the detection marker horseradish peroxidase or soybean peroxidase. Binding of the labeled third member to the electrode via the second member results in electrical contact between the peroxidase and the redox polymer, causing the electrical connection of the reaction centers of the peroxidase label to the electrode through the conducting redox polymer. Such connection converts the film to a catalyst for the electroreduction of the hydrogen peroxide produced within the film by the immobilized substrate-generating enzyme.

DETAILED DESCRIPTION OF THE INVENTION

Definitions

As used herein, the following terms and phrases have the definitions indicated:

Redox Hydrogel: The hydrated form of a crosslinked redox polymer.

Substrate generating enzyme: An enzyme generating or producing the substrate of a detection marker, generally immobilized in the redox hydrogel. The detection marker is usually an enzyme and is covalently bound to the third member. An example of substrate generated by the enzyme is $H_2O_2$. $H_2O_2$ is generated, for example, by the substrate generating enzyme choline oxidase, which catalyzes the reaction of $O_2$ and choline. Substrate generating enzymes that do not exchange electrons with the redox polymer at the potential where the electrode is poised are preferred. Electron exchange means transfer of electrons from the enzyme to the redox hydrogel or from the redox hydrogel to the enzyme.

Binding Agent: A macromolecular binding agent of a biomolecule. Examples of binding agents include avidin; streptavidin; single stranded (ss) oligonucleotides; single stranded DNA; and peptide oligonucleotides or peptide DNA. The binding agent is immobilized in or on the redox hydrogel.

First member of the ligand—ligand receptor pair: A molecule binding to the binding agent and to the second member of the pair; or a molecule bound to the redox hydrogel and binding to the second member. The first and third members are not identical. An example of a first member is a biotinylated antigen.

Second member of the ligand—ligand receptor pair: Binds to the first and third members. An example of a second member is an antibody or an $F(ab')_2$ fragment of an antibody against both the antigen of the first member and the antigen of the third member. The electrochemical affinity assay of this invention is usually of the second member.

Third member labeled with the Detection Marker: Binds to the second member and is labeled with a detection marker, which is preferably a catalyst, such as an enzyme, and most preferably an oxidoreductase. An example of a third member is a peroxidase-labeled antigen.

Detection Marker: A catalyst, usually an enzyme and preferably an oxidoreductase, labeling the third member. The detection marker can transfer electrons to or accept electrons from the redox hydrogel on the electrode. In these processes the detection marker is electrooxidized or electroreduced. When electrooxidized, the detection marker can oxidize a detection compound. When electroreduced, it can reduce a detection compound.

Detection Compound: A molecule or ion, or a precursor of a molecule or ion, the electrooxidation or the electroreduction of which produces the detected electrochemical signal, usually a current or potential. The detection compound is electrooxidized or electroreduced in the redox polymer film. An example of an electroreduced detection compound is hydrogen peroxide.

Figure 1A:
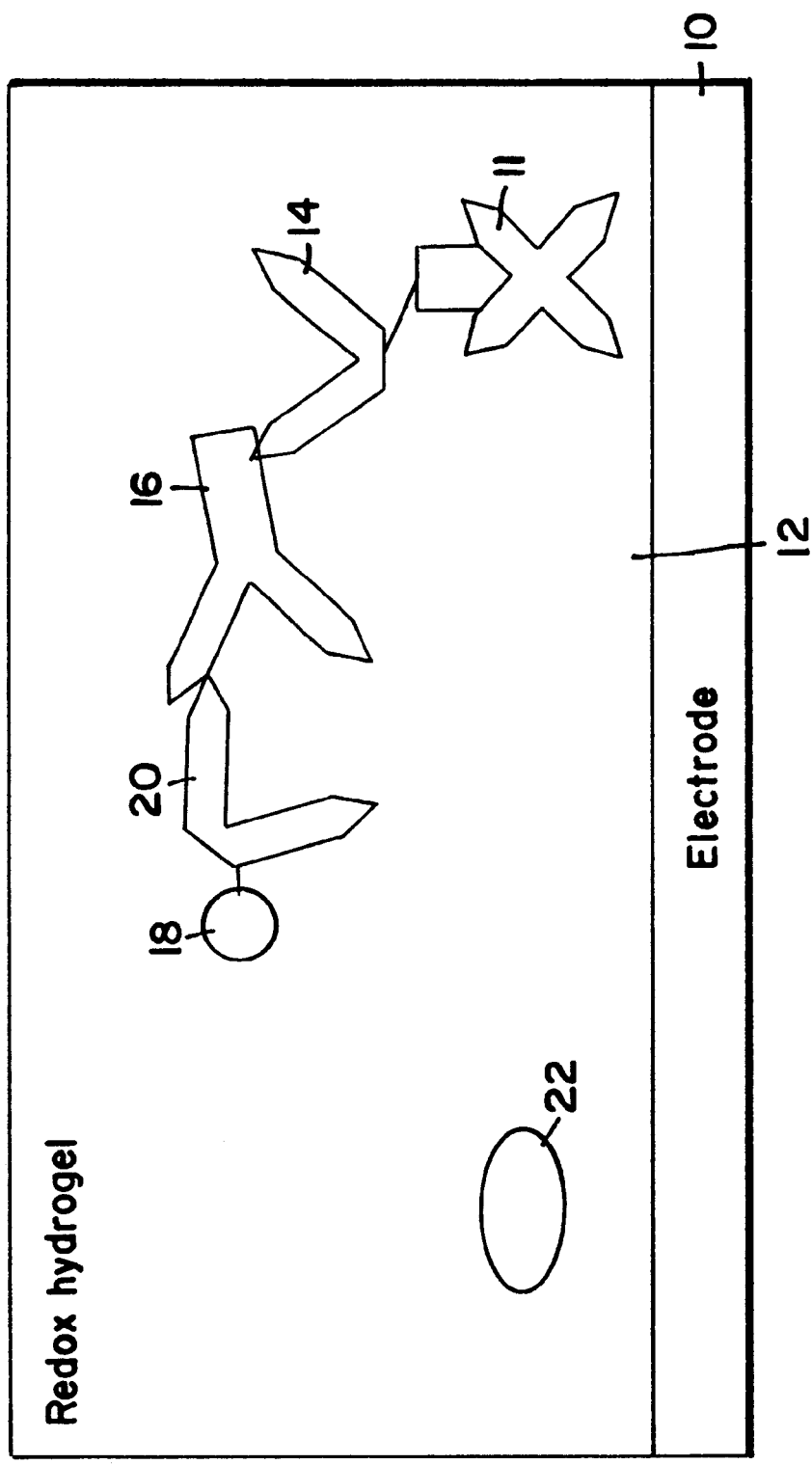
FIGS. 1A and 1B are schematic diagrams showing the transduction of the concentration of a second member of a ligand—ligand receptor pair, IgG, to a cathodic current.
Figure 1B:
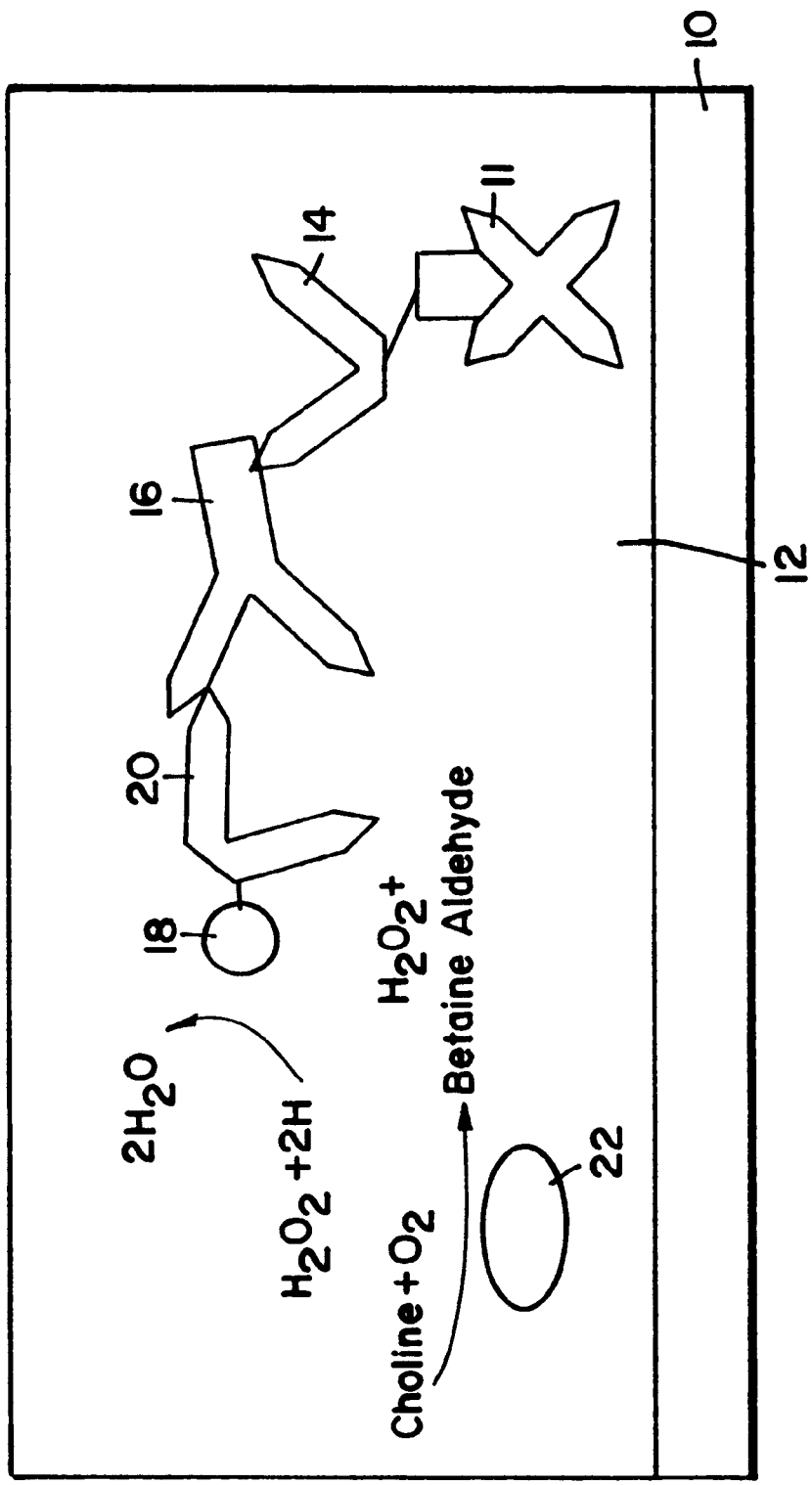

As shown schematically in FIGS. 1A and 1B, an affinity assay of the invention includes an electrode 10 coated with a redox polymer 12, preferably a redox hydrogel, in which the first member 14 is immobilized via a binding agent 11 such as avidin. The binding agent 11 is preferably covalently bound to the redox polymer 12.

In the assay of the invention, a second member 16 of the ligand—ligand receptor pair is conjugated with and thereby bound to the first member 14; then the second member 16 is conjugated with and bound to the third member 20. The third member 20 is labeled with a detection marker 18. In a "sandwich" type immunoassay, the second member is an antibody. It can, however, also be an antigen, if the first and third members are non-identical antibodies to the different regions of the second member antigen. The redox hydrogel 12 further includes at least one substrate-generating enzyme 22, meaning an enzyme generating the detection compound. It is preferred, though not required, that the reaction centers of the substrate generating enzyme 22 not be reduced by the reduced redox centers of the redox polymer, nor oxidized by the oxidized redox centers of the redox polymer, when the redox polymer film 12 is in contact with the electrode 10 and the electrode is poised at its operating potential. The detection compound is, preferably, the substrate of the detection marker 18, which is preferably an oxidoreductase. Binding of the first member 14 to the second member 16, and of the second member 16 to the third member 18, results in an increase in the current passing through the electrode. The increase in current is caused by the catalysis of the electrochemical reduction or oxidation reaction of the detection compound in the combined presence of the detection marker 18 and the redox hydrogel 12 on the electrode. The increase in current correlates with the binding of the second member 16 of the ligand pair, and thereby with the amount of the second member 16 in a sample. This preferred assay system does not require separation or washing steps, permitting use of the assay system in situ in biological fluids. The assay can be carried out in colored and light-scattering media like blood and in media where externally added detection compounds, like hydrogen peroxide, rapidly decompose. In the instant assay hydrogen peroxide is generated in the film on the electrode and is available, at least in part, for electroreduction when the film becomes electrocatalytic through the immobilization of the detection marker, which is bound to the third member.

Figure 2:
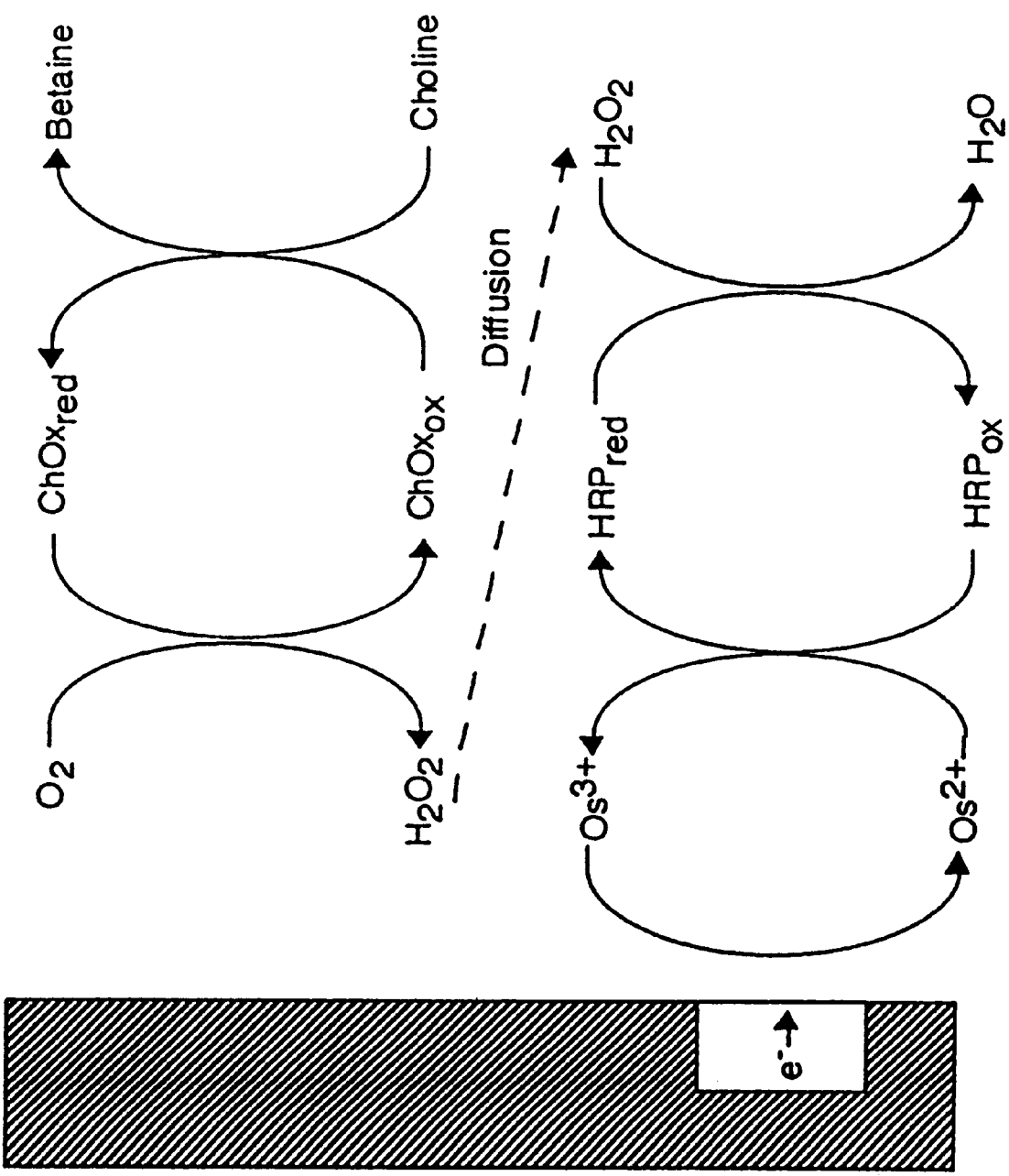
FIG. 2 is a schematic diagram showing electron transport on binding of the enzyme labeled third member in an immunoassay of the invention.

FIG. 2 shows schematically the flow of electrons in an affinity assay system of the invention. Choline oxidase, a substrate generating enzyme 22, present in the redox polymer 12, generates hydrogen peroxide in the redox hydrogel 12. Binding of a peroxidase-labeled third member 20 to the immobilized second member 16 of a ligand—ligand receptor pair enables peroxidase-catalyzed electroreduction of hydrogen peroxide, a reaction where electrons flow from the electrode 10 to the redox hydrogel 12; from the redox hydrogel 12 to the peroxidase; and from the peroxidase to hydrogen peroxide, the hydrogen peroxide being electroreduced to water.

The Working Electrode

The working electrode 10 is typically a thin film of conductive material disposed on an insulating substrate. Suitable materials for the substrate include, for example, insulating silicon, fused silicon dioxide, silicate glass, alumina, aluminosilicate ceramic, an epoxy, an epoxy composite such as glass fiber reinforced epoxy, polyester, polyimide, polyamide, or polycarbonate.

A variety of conductive materials can be used to form the working electrode 10. Suitable materials include, for example, carbon, conductive polymers, and metals. Examples of useful metals include gold, platinum, palladium, tantalum, tungsten, and their alloys, as well as metallic compounds like titanium nitride, and ruthenium dioxide. The preferred conductors do not corrode rapidly in aerated aqueous 0.1 M NaCl near neutral pH when a potential of 0.2 volts positive of the potential of the saturated calomel electrode (SCE) is applied. The corrosion current density is preferably less than $10^{-4}$ A cm$^{-2}$, and more preferably less than $10^{-7}$ A cm$^{-2}$.

Thin films of these materials can be formed by a variety of methods including, for example, sputtering, reactive sputtering, physical vapor deposition, plasma deposition, chemical vapor deposition, printing, and other coating methods. Discrete conductive elements may be deposited to form each of the working electrodes, for example, using a patterned mask. Alternatively, a continuous conductive film may be applied to the substrate and then the working electrodes can be patterned from the film.

Patterning techniques for thin films of metal and other materials are well known in the semiconductor art and include photolithographic techniques. An exemplary technique includes depositing the thin film of conductive material and then depositing a layer of a photoresist over the thin film. Typical photoresists are chemicals, often organic compounds, that are altered by exposure to light of a particular wavelength or range of wavelengths. Exposure to light makes the photoresist either more or less susceptible to removal by chemical agents. After the layer of photoresist is applied, the photoresist is exposed to light, or other electromagnetic radiation, through a mask. Alternatively, the photoresist is patterned under a beam of charged particles, such as electrons. The mask may be a positive or negative mask depending on the nature of the photoresist. The mask includes the desired pattern of working electrodes, which are the electrodes on which the electrocatalytic reactions take place when the detection marker and the redox hydrogel are both present and immobilized on the electrode. Once exposed, the portions of the photoresist and the thin film between the working electrodes is selectively removed using, for example, standard etching techniques (dry or wet), to leave the isolated working electrodes of the array.

The working electrode 10 can have a variety of shapes, including, for example, square, rectangular, circular, ovoid, and the like. The working electrode may have dimension (e.g., length, width, or diameter) which can be 50 µm or less. In some embodiments, the working electrodes are three dimensional structures, and can have a surface area of $1 \times 10^{-4}$ cm$^2$ or less. Multiple electrodes may be used in an array.

Counter and reference electrodes may be present in the electrolytic solution off the surface of the substrate containing the working electrode. Alternatively, the counter and reference electrodes may be formed on the substrate containing the working electrode, for example, located on the same or a different surface as the working electrode. It is not necessary for each working electrode to have a dedicated counter electrode or reference electrode. The same counter or reference electrode can serve multiple, or even all, electrodes of an array. A single electrode, such as an Ag/AgCl electrode, can serve as both counter and reference electrode. Preferably the reference electrode is one that does not leach ions and maintains a constant potential. The reference electrode can be, for example, a silver wire or structure, in contact with the electrolytic solution. The surface of the silver wire or structure can be partially oxidized to produce AgCl chemically, or electrochemically.

The Redox Polymer

The electrode is coated with a thin film of a redox polymer 12. The redox polymer 12 is deposited on the electrode 10. When multiple working electrodes are used, redox polymer 12 is not deposited on the substrate between the electrodes 10, thus maintaining the electrical isolation of the working electrodes of each other. Another specific method whereby a redox polymer can be deposited, exclusively on the electrode, is electrophoresis. This is a preferred method for coating electrodes of an array when their diameter is small, usually smaller than 50 µm.

Redox hydrogels are formed of the crosslinked redox polymers upon their immersion in aqueous solutions. The redox hydrogels provide for transport of electrons between the electrode and the detection marker. One type of redox polymer is a redox hydrogel which typically contains at least 10% of water. Water soluble molecules usually permeate through the redox hydrogel rapidly. Electron conduction in the redox hydrogel is believed to occur through electron exchange between polymer segments that, being tethered, do not leach out but are nevertheless mobile within a limited, small radius.

In general, the redox polymer includes electroreducible and electrooxidizable functions, termed redox centers. These have redox potentials that are a few hundred mV above or below the redox potential of the standard calomel electrode (SCE). Preferably, the redox centers of the potentials of the polymers are not more reducing than about −400 mV and not more oxidizing than about 800 mV versus SCE, and most preferably are not more reducing than about −150 mV and not more oxidizing than about +400 mV versus SCE at neutral pH. The most preferred redox polymers have osmium, ruthenium, or cobalt redox centers and a redox potential ranging from about −150 mV to about +400 mV versus SCE.

In general, redox polymers suitable for use in the invention have bonds or charges that prevent, or substantially reduce, the diffusional outflux or loss of the redox species during the period of time in which the sample is being analyzed. The bond between the redox species and the polymer may be covalent, coordinative, or ionic. Useful redox polymers and methods for producing them are described in U.S. Pat. Nos. 5,264,104; 5,356,786; 5,262,035; 5,320,725; and 5,665,222, incorporated herein by reference. Although many organic or organometallic redox centers can be incorporated in or bound to a polymer and used in the system of the present invention, the preferred redox species are transition metal complexes. The more preferred transition metal complexes are osmium, ruthenium, iron, and cobalt compounds or complexes. The most preferred are osmium and ruthenium complexes.

One type redox polymer contains a redox species covalently bound to a polymer. An example of such a polymer is poly(vinylferrocene). Another type of redox polymer contains an electrostatically bound redox species. Typically, this type of redox polymer comprises a charged polymer coupled to an oppositely charged redox species. Examples of this type of redox polymer include a negatively charged polymer such as Nafion® (DuPont) in which a positively charged redox species, containing one or more of osmium or ruthenium polypyridyl cations is distributed. Another example of such a polymer is a polymer comprising positively charged functions, such as quaternized poly(4-vinyl pyridine) or poly(1-vinyl imidazole), and negatively charged redox species such as ferricyanide and ferrocyanide. The redox polymer may consist of a highly charged redox species, that itself may be polymeric and have multiple redox centers and an oppositely charged polymer, the redox polymer being bound electrostatically within.

In another embodiment of the invention, suitable redox polymers include a redox species coordinatively bound to a polymer. For example, the redox species may be formed by complexing of osmium, ruthenium or cobalt ions with 2,2'-bipyridyl and also with poly(1-vinyl imidazole) or poly (4-vinyl pyridine) or with a copolymer of either of these.

The preferred redox species are complexes of transition metals, most preferably complexes of osmium, ruthenium, or cobalt. The complexes comprise one or more heterocyclic ligands, each ligand having two or more rings, each ring with one or more nitrogen atoms, such as 2,2'-bipyridine, 1,10-phenanthroline, 2,2',2''-terpyridine, or derivatives thereof. More preferred complexes include osmium cations complexed with two ligands, each ligand containing 2,2'-bipyridine, 1,10-phenanthroline, or derivatives thereof, the two ligands not necessarily being the same. In the preferred complexes of osmium, ruthenium, or cobalt, three or more of the coordination sites of the metal ion are nitrogen-occupied, and the number of ligands ranges from 1 to 3. In the most preferred complexes, five of the coordination sites are nitrogen-occupied, and the number of ligands ranges from 2 to 3.

The preferred redox species exchange electrons rapidly with each other, in a process known as self-exchange and also with the working electrode, so that the complexes can be rapidly electrooxidized and electroreduced. While they can be electrostatically held in the redox polymer, the preferred redox species are coordinatively or covalently bound to the polymer. Those of the preferred polymers that bind the ions of the metal ion complex coordinatively have nitrogen-containing heterocyclic rings, such as pyridine, imidazole, or derivatives thereof. These bind, as ligands, to the cations of the redox species.

Preferred polymers for complexation with redox species, such as the osmium complexes, described above, include polymers and copolymers of poly(I-vinyl imidazole) (referred to as "PVI"), poly(4-vinyl pyridine) (referred to as "PVP"), and pyridinium-modified modified poly(acrylic acid). Suitable copolymer substituents of poly(1-vinyl imidazole) include acrylonitrile, acrylamide, acrylhydrazide, and substituted or quaternized N-vinyl imidazole. The osmium complexes coordinatively bind with the imidazole and pyridine groups of the polymer. In copolymers comprising non-coordinating mers, or weakly coordinating ones, such as acrylamide or acrylonitrile, and also strongly coordinating mers such as N-vinyl-imidazole or 4-vinylpyridine, the ratio of osmium complexes to imidazole and/or pyridine groups ranges from 1:10 to 1: 1, preferably from 1:2 to 1: 1, and more preferably from 3:4 to 1:1. Also, the preferred ratio of the number of complexed transition metal atoms and polymerized vinyl functions ranges from about 1:2 to about 1:30, and more preferably from about 1:5 to about 1:20.

Examples of other redox species include quinones and species that in their oxidized state have quinoid structures, such as Nile blue and indophenol. The preferred quinones and quinoids do not have hydrogen atoms in their six-membered rings.

The redox polymer 12 also preferably includes a binding agent 11 for binding the first member 14 of the ligand—ligand receptor pair. In a preferred embodiment the binding agent 11 is avidin or streptavidin. It binds to the biotinylated first member 14 thereby immobilizing the first member 14 on the electrode.

The binding agent 11 is preferably covalently bound to the polymer, for example by carbodiimide coupling of carboxylate functions of avidin or streptavidin, to hydrazide functions on the polymer. When the binding agent 11 is an oligonucleotide or DNA, carbodiimide and similar coupling agents activate preferably a terminal phosphate function of these molecules enabling their covalent binding to hydrazide functions of the polymers like PAH of FIG. 3.

Alternatively, the first member 14 can be bound directly, preferably covalently, to the redox polymer by a method such as carbodiimide coupling.

In one embodiment, the polymer is a copolymer of PVI or PVP with polyacrylamide (it is referred to as "PAA") in which $Os(bpy)_2 Cl^{+/2+}$ is coupled to the imidazole or pyridine functions respectively. To form hydrazides in this redox polymer, for subsequent covalent attachment of the binding agent 11 or for attachment of first member 14, a portion of the amide functions is converted to hydrazide functions by reaction with hydrazine, according to known processes. Typically, at least 5% of the amide groups are converted, preferably, at least 10% of the groups are converted, and more preferably, at least 20% of the groups are converted. The ratio of hydrazide-modified amide groups to unmodified amide groups of the resulting polymer is typically 1:1 to 1:20, and preferably 1:2 to 1:10. The ratio of PVI or PVP to PAA is typically 5:1 to 1: 15, preferably, 2:1 to 1: 12, and, more preferably, 1:1 to 1:10. The PAA copolymer in which part of the amides is converted to hydrazides is termed PAH.

In another embodiment, the polymer is a modified poly (acrylic acid). A portion of the carboxylic acid functions of the poly(acrylic acid) are converted to pyridine or imidazole carrying functions. These can be amides, such as those formed with 4-(aminoalkyl)-pyridine, particularly 4-(2-aminoethyl)-pyridine, that can be covalently attached through carbodiimide coupling. The pyridine and imidazole groups can then be used for coordinative binding with the osmium complexes. Typically, at least 2%, preferably, at least 5%, and, more preferably, at least 10%, of the carboxylic acid functions are converted to functions with pyridine or imidazole rings. At least a portion of the remaining carboxylic acid groups are converted to hydrazide groups for crosslinking redox polymer and for covalent attachment of the binding agent or of the first member. Typically, at least 2%, preferably, at least 5%, and, more preferably, at least 10%, of the residual carboxylic acid groups are converted to hydrazide groups.

A variety of methods may be used to immobilize a redox polymer on an electrode surface. One method is adsorptive immobilization. This method is particularly useful for redox polymers with relatively high molecular weights, for example, greater than about $10^4$ daltons, preferably greater than $10^5$ daltons, and most preferably greater than $10^6$ daltons. The molecular weight of a polymer may be increased, for example, by cross-linking with a di- or polyfunctional cross-linking agent, such as those listed in the Pierce catalog, 1994, pages TI55-Ti67. Examples of functions of cross-linking agents useful in the invention include epoxy, aldehyde, N-hydroxysuccinimide, halogen, imidate, thiol, and quinone functions. Examples of crosslinkers include poly(ethylene glycol) diglycidyl ether and cyanuric chloride, poly(ethylene glycol) diglycidyl ether (PEGDGE) of 400 or 600 daltons being most preferred. Other cross-linking agents may also be used.

In another embodiment, the redox polymer is immobilized by covalent bonding to a functionalized electrode surface. Carbon surfaces can be modified for covalent attachment of a redox polymer, for example, by electroreduction of a diazonium salt or by oxidation with hydrogen peroxide in the presence of divalent iron ions at a pH of less than 6. As an illustration, reduction of a diazonium salt formed upon diazotization of p-aminobenzoic acid modifies a carbon surface with phenylcarboxylic acid groups. These groups can then be activated by a carbodiimide, such as 1-ethyl-3-(3-dimethylaminopropyl)-carbodiimide hydrochloride. The activated groups are then bound with a hydrazide or amine-functionalized redox couple, such as, for example, PAH, the polymer of FIG. 3.

The preferred redox hydrogel 12 contains also additional compounds that are useful in the affinity assay of the invention. In particular, it contains the substrate generating enzyme 22. This enzyme catalyzes the generation of the detection compound, which is the substrate of the detection marker 18. The enzyme generates the detection compound by reacting stable and preferably non-toxic reagents. As a result of the internal generation of the detection compound, within the film on the electrode, the need for adding unstable or toxic agents to the analyzed fluid is obviated. This enables the affinity assay of whole blood, for example, where the detection compound, meaning the or substrate of the detection marker of the third member, like hydrogen peroxide, would rapidly decompose.

An example of a substrate generating enzyme that may be immobilized in the redox polymer is choline oxidase, which generates hydrogen peroxide in situ within the redox polymer film on the electrode. Hydrogen peroxide is catalytically electroreduced when the peroxidase detection marker of the third member is in contact with the redox hydrogel. While in absence of either the peroxidase detection marker or the redox polymer, the film is not electrocatalytic for $H_2O_2$ reduction in the applied potential range between 0.1 V (SCE) and +0.4 V (SCE), the film is electrocatalytic through this range when both the peroxidase and the redox polymer are co-immobilized. The redox or reaction centers of choline oxidase do not rapidly exchange electrons with those of the redox hydrogel, so the presence of the enzyme in the hydrogel and the presence of choline do not change the signal, usually the current or potential. Choline oxidase catalyzes the reaction of molecular oxygen with choline, whereby hydrogen peroxide and betaine aldehyde are formed.

Ligand—ligand Receptor Pair

A ligand—ligand receptor pair, consisting of the first member and the second member, includes any such pair known to bind with specificity. Such ligand—ligand receptor pairs are well known and include the following: antigen-antibody; peptide, e.g. growth factor-receptor; nucleic acid-nucleic acid binding protein; complementary pairs of nucleic acids; and of peptide nucleic acids and nucleic acids.

When an antibody is used, it is possible to use a fragment, such as an $F(ab')_2$ fragment. When a nucleic acid sequence is used, an oligonucleotide of less than about 200 nucleotides is preferred.

The first member 14 of the ligand—ligand receptor pair is immobilized on the electrode 10, by either covalent attachment to the redox polymer 12, and more preferably, through non-covalent affinity binding with binding agent 11.

The second member 16 of the ligand—ligand receptor pair binds the first member 14. Suitable reaction conditions for such binding are known in the art and vary with the nature of the particular pair used.

The Third Member and Its Detection Markers

The third member 20 and the second member 16 are also a ligand receptor-ligand pair. Again, any such pair known to bind with specificity can constitute the pair.

Useful detection markers are known, and include catalysts which accelerate the oxidation or reduction, preferably the electrooxidation or electroreduction by the electrooxidized or electroreduced redox polymer, of the detection compound. The acceleration of the electrochemical reaction results in an increase in the current at the electrode, the charge flowing usually via the redox polymer and the catalyst. When a third member 20 is labeled with the detection marker 18 and when it binds to the immobilized second member 16, the current generated at the electrode is increased through electrocatalysis of a reaction of the detection compound.

The preferred affinity assays of the invention are rapid, specific, efficient, and operate with a high signal to noise ratio, preferably greater than 10. The scheme of an exemplary "sandwich" type immunoassay is shown in FIGS. 1A and 1B and is demonstrated below in Example 1. It operates with a signal to noise ratio of about 15.

The preferred affinity assay of the invention can be performed either with no additive to the biological fluid analyzed or with adding only a non-toxic biochemical such as choline. The assay can also be performed in an opaque, colored or light-scattering medium, such as blood; and in the preferred mode it requires no separation or washing steps.

Preferred Operation and Practice of the Assay

In the preferred mode of operation, the electrode 10 is coated with the crosslinked redox polymer 12 containing the binding agent 11 and the substrate generating enzyme 22, both covalently bound within the redox hydrogel 12. The first member 14 is then bound to the redox polymer 12. This completes the preparation of the electrode for the assay. The electrode is then immersed in the fluid to be assayed for the presence and/or amount and/or concentration of the second member. It is preferred that during this immersion the fluid be moving relative to the electrode, meaning that either the electrode be moving, for example rotating, in the fluid, or that the fluid be flowing when the electrode is stationary. After, or simultaneously with, binding of the second member 16 to the electrode via the affinity reaction with the first member 14, the electrode is exposed to the third member 20. The electrode is poised at a potential where the electrocatalytic reduction or oxidation of the detection compound proceeds, this electrode reaction being catalyzed when the detection marker contacts the redox polymer 12, such contact being made upon the binding of the third member 20 to the second member 16.

The Detection Marker of the Third Member

A variety of catalysts can be used as the detection marker 18. Exemplary catalysts are enzymes that catalyze an electrochemical reaction of a detection compound. A variety of enzymes are useful including, for example, peroxidases for use with hydrogen peroxide, glucose oxidase and glucose dehydrogenase for use with glucose, and lactate oxidase and lactate dehydrogenase for use with lactate. While in the case of hydrogen peroxide the detection compound is catalytically electroreduced and is internally generated in the film, in the case of glucose or lactate, which are abundant in biological fluids like blood, the detection marker is externally supplied. Also, these detection compounds are catalytically electrooxidized when both the glucose oxidase detection marker or the lactate oxidase detection marker is immobilized in or on the redox polymer film and the electrode is poised at a potential between −0.3 V (SCE) and +0.7 V (SCE), preferably −0.2 V (SCE) and +0.5 V (SCE) and most preferably −0.1 V (SCE) and +0.3 V (SCE). Preferably, thermostable enzymes (enzymes capable of operation for at least 1 hour at 37° C.) are used. Soybean peroxidase is one example of a thermostable enzyme.

The Detection Compound

The detection compound is a substrate for the detection marker or a precursor of the substrate of the detection member. For example, hydrogen peroxide is a detection compound which is a substrate for the detection marker, peroxidose.

EXAMPLES

The invention may be better understood by reference to the following examples, which are not intended to limit the scope of the invention.

Example 1

Figure 3:
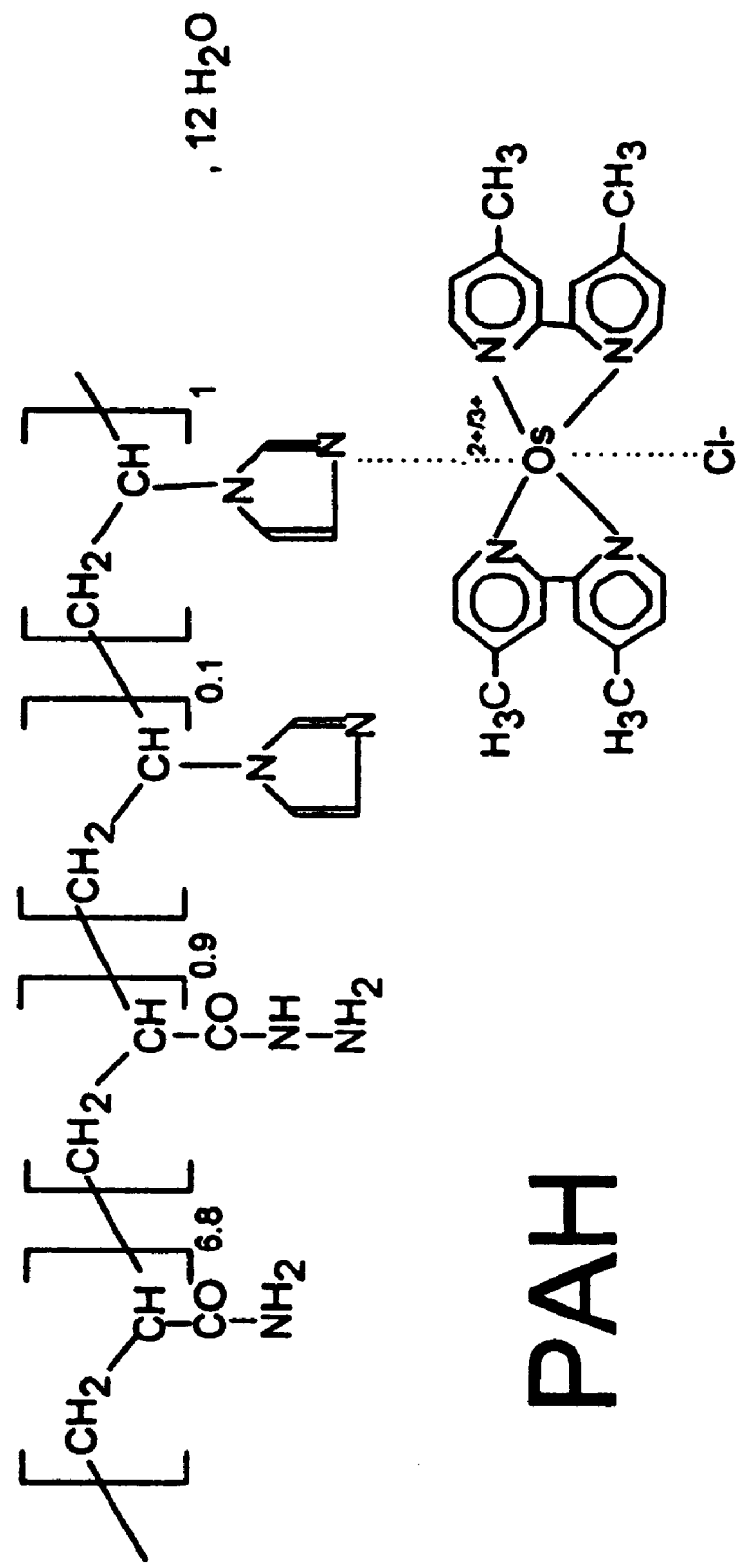
FIG. 3 is a diagram showing the structure of the redox polymer PAH which forms an electron-conducting hydrogel upon crosslinking.

Electrochemical ELISA A non-competitive, sandwich type ELISA was started by immobilizing the redox polymer PAH onto a glassy carbon electrode. PAH was made as described in de Lumley-Woodyear et al., 1995, *Anal. Chem.* 67:1332–1338. The structure of the polymer is shown in FIG. 3.

Standard coatings were formed by mixing 2.5 parts of polymer (5 mg/ml in water); 1.5 parts poly(ethylene glycol 400 diglycidyl ether (PEGDGE) (0.5 mg/ml in water) (technical grade, Polysciences, #08210); 1.0 parts choline oxidase (20 mg/ml in 0.1M $NaHCO_3$) (Sigma #C-5896); and 4 parts avidin (5 mg/ml in 0.1 M $NaHCO_3$) (Sigma #A-9390). A volume of 3 microliters of this solution was applied to the 3 mm diameter glassy carbon electrode. The films were permitted to cure and crosslink for 48 hours in a humid atmosphere and then allowed to dry overnight in air prior to testing.

The electrodes, containing avidin (binding agent) and choline oxidase (substrate generating enzyme) immobilized within their redox polymer coating, were washed in Dulbecco's PBS for 15 minutes to rehydrate the polymer hydrogel and to remove any non-covalently bound avidin or choline oxidase. PBS, the pH 7.4 phosphate buffer solution, was made with the sodium (0.008 M) and potassium (0.002 M) phosphate and with sodium (0.114 M) and potassium (0.01 M) chlorides. The rehydrated electrodes were then soaked in 5 ml PBS containing 9 micrograms of biotin-labeled anti-rabbit IgG (first member of the ligand—ligand receptor pair) for 30 minutes, followed by washing 10 minutes in PBS to remove any unbound biotin-anti-IgG. This completed the preparation of the electrode for the assay of rabbit IgG.

The completed electrodes were then placed in a test cell containing 17.5 ml of 20 mM choline in PBS and a potential of −70 mV vs SCE was applied. The electrodes were rotated at 1000 rpm. A sample amount of IgG (second member of the ligand—ligand receptor pair) was added, and the mixture permitted to incubate for 30 minutes. At the end of the incubation period, 6.0 micrograms of HRP-labeled anti-rabbit IgG (third member, labeled with detection marker) was added and the resulting increase in reduction current was monitored. The currents were recorded 30 minutes after the addition of the HRP-labeled probe.

Figure 4:
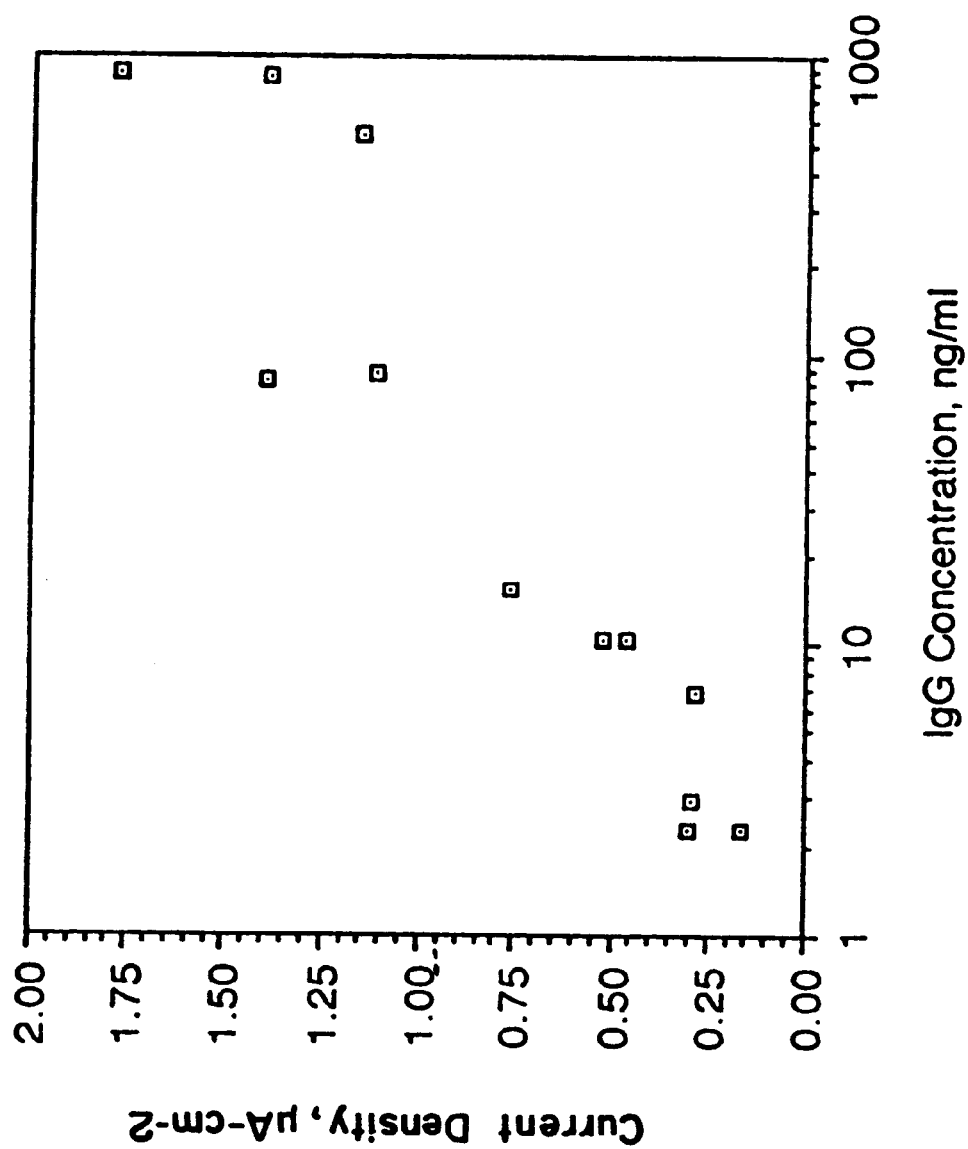
FIG. 4 is a graph showing the dependence of the current density on the concentration of the second member of the ligand—ligand receptor binding pair, IgG.

FIG. 4 shows the dependence of the hydrogen peroxide electroreduction current on the concentration of the ligand, rabbit IgG. The current increased linearly, with the rabbit IgG concentration over the 1–1000 ng/ml range. A linear regression analysis of the data yielded an $R^2$ value of 0.89 and a negative current at the intercept where the rabbit IgG concentration was nil, suggesting that some rabbit IgG was lost from the solution through adsorption on the untreated wall of the Pyrex glass test cell.

Figure 5:
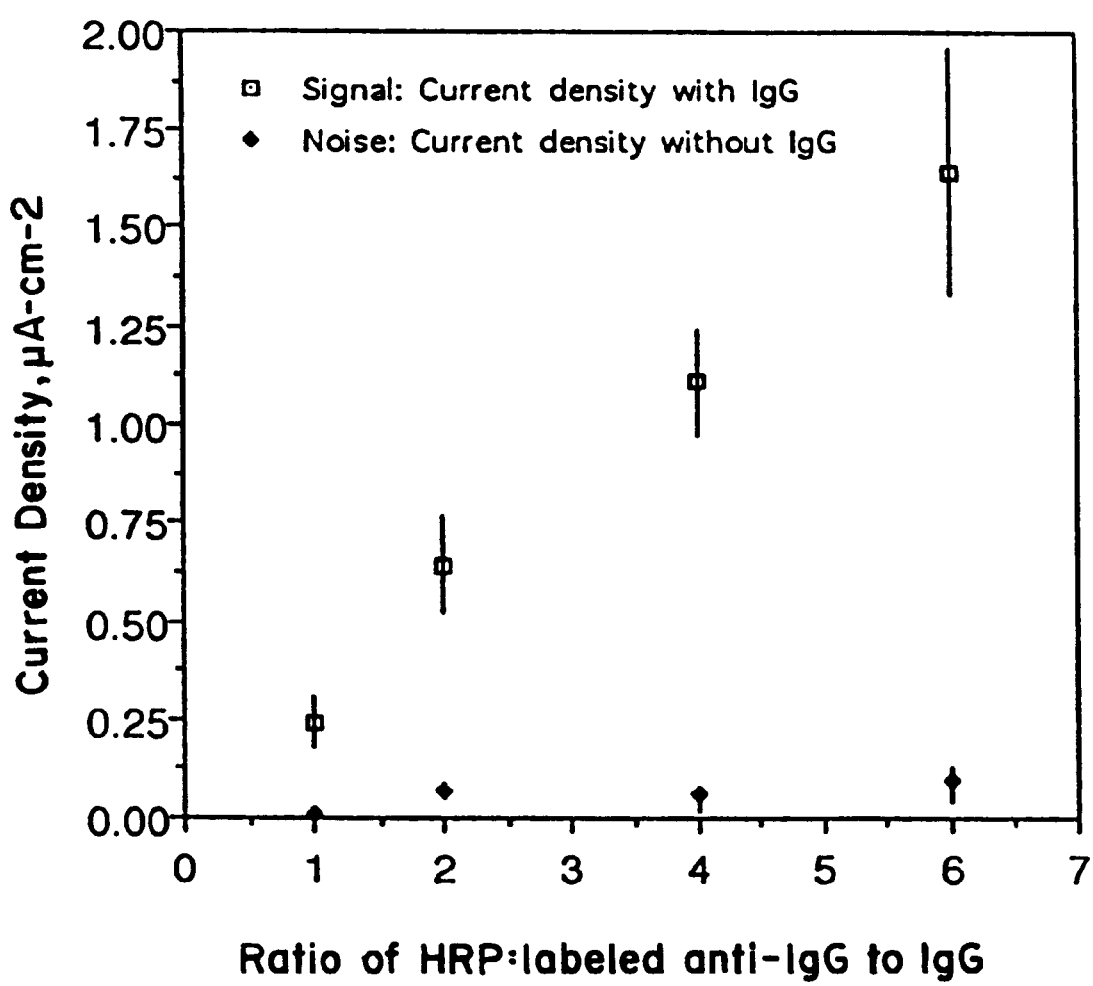
FIG. 5 is a graph showing the dependence of the current density on the ratio of the third member, HRP-labeled anti-IgG to the second member, IgG at a fixed concentration of IgG (86 ng/ml).

To assess the dependence of the signal-to-noise ratio on the concentration of the HRP-labeled anti-rabbit IgG probe, the dependence on the current density on the molar ratio of HRP labeled anti-rabbit IgG probe to the ligand IgG was determined. As shown in FIG. 5, in the absence of ligand IgG there was very little noise associated with non-specific binding of the HRP-labeled anti-rabbit IgG probe. At a 4:1 ratio, the signal (specific binding) to noise (non-specific binding) ratio was 15. The results of the ensemble of control experiments, in which individual components of the test system were deleted, are shown below in Table 1.

TABLE 1

| Electrode Constituents | | | | Antigen | Antibodies | | | |
|---|---|---|---|---|---|---|---|---|
| Polymer | PEGDGE 400 | Choline Oxidase | Avidin | Rabbit IgG | Biotin: Ab | HRP: Ab | Reagents Choline | Signal $\mu A/cm^2$ |
| + | + | − | + | + | + | + | + | 0 |
| + | + | + | − | + | + | + | + | 0.12 |
| + | + | + | + | − | + | + | + | 0–0.1 |
| + | + | + | + | + | − | + | + | 0.17 |
| + | + | + | + | − | + | − | + | 0.03 |
| + | + | + | + | − | − | − | + | 0.03 |
| − | − | − | − | + | − | + | − | 0 |
| − | − | − | − | − | − | − | + | 0 |
| + | + | + | + | + | + | + | + | 1.03 |
| + | + | + | + | + | + | + | + | 1.06 |

The residual current density, following deletion of any of the essential components, was equal to or smaller than the current density when the analyte itself (rabbit IgG) was absent. In the presence of choline, but without any immunoreagent, the current density was only 0.03 $\mu A/cm^2$, showing, as expected, that choline oxidase was so poorly "wired", if at all, that electroreduction of choline did not interfere with the assay. When the avidin-containing redox hydrogel was not activated with biotin-labeled anti-rabbit IgG, the current density was 0.17 $\mu A/cm2$, about one fifth of that observed in a typical assay.

Figure 6:
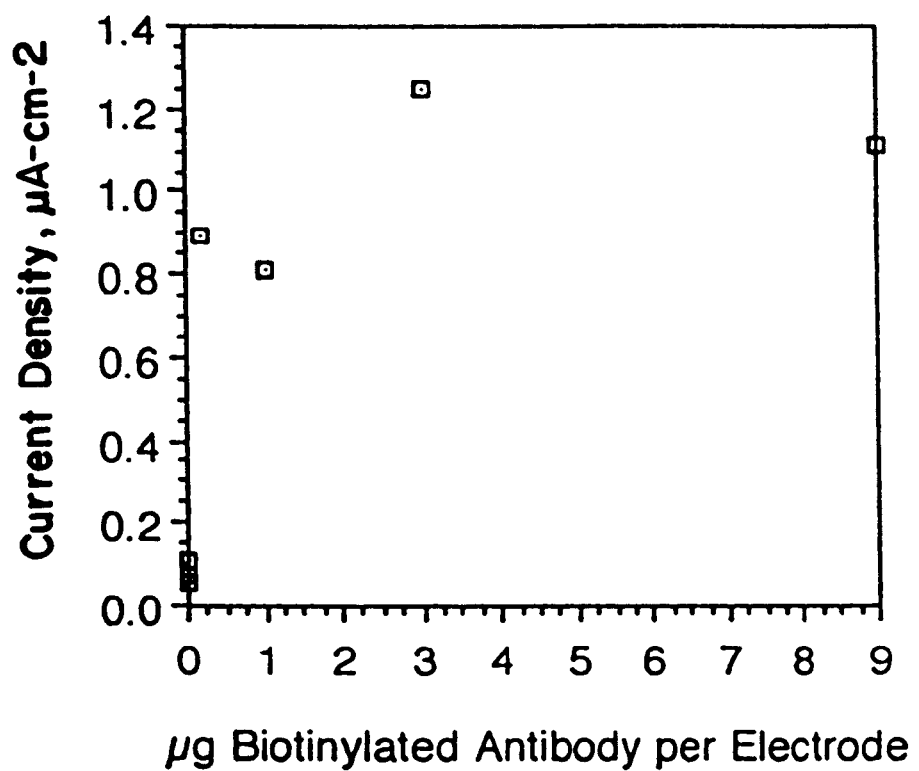
FIG. 6 is a graph showing the dependence of the current density on the loading of the first member, biotin-labeled anti-rabbit IgG on the redox-polymer film on the electrode at a fixed concentration of IgG (86 ng/ml).
Figure 7:
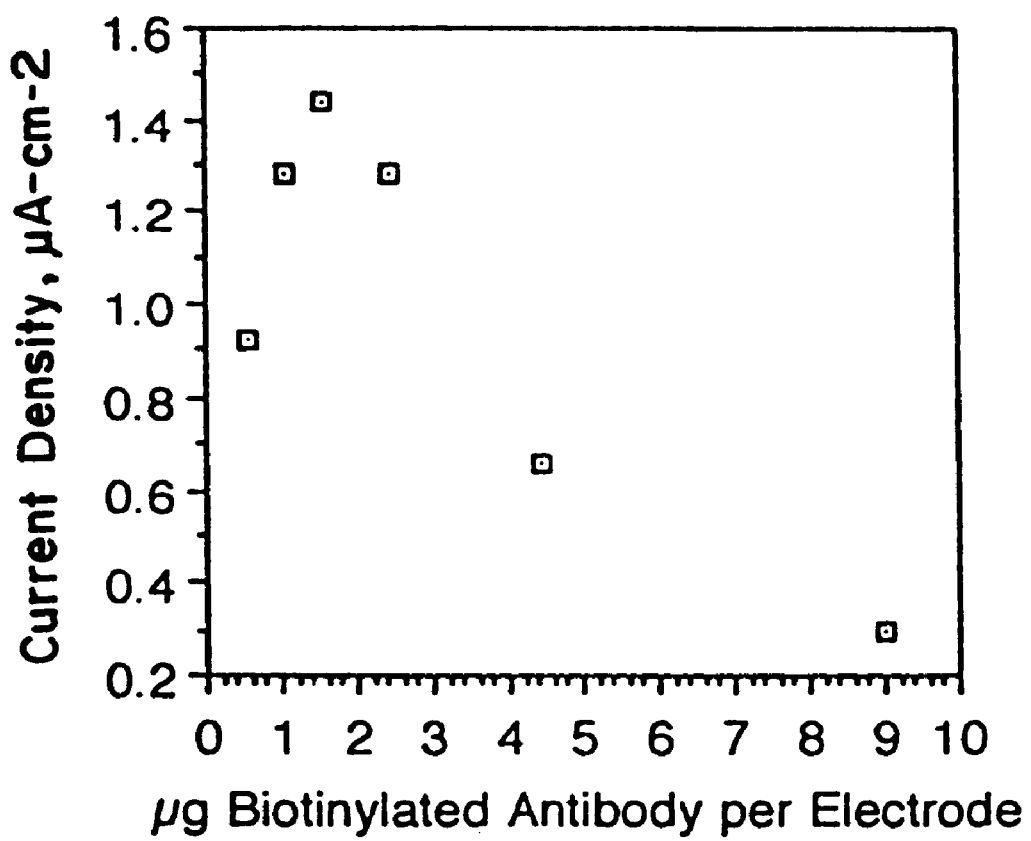
FIG. 7 is a graph showing the dependence of the current density on the concentration of choline, the non-toxic and stable precursor of the detection compound, $H_2O_2$.

The dependence of the current density on the biotin-labeled anti-rabbit IgG loading of the electrodes is shown in FIG. 6.

In a separationless assay when the concentration of the rabbit IgG, $F(ab')_2$ fragments was 86 mg/mL and the concentration of the HRP-labeled anti-rabbit IgG was 344 mg/mL. (HRP is horseradish peroxidase), and with only choline added to the test solution, a current density of 1.5 $\mu A\ cm^{-2}$ was observed.

Varying the ionic strength of the test buffer influenced the level of both the signal and the noise. Both signal and noise decreased rapidly as salt content increased, with the noise level dropping to essentially zero for salt concentrations of 0.2 M and above.

When the $F(ab')_2$ antibody fragments were replaced with whole antibodies, the signal to noise ratio was about 4:1 under identical conditions.

Study of the effect of the duration of the steps of (a) the activation with biotin-labeled anti-rabbit IgG, (b) the binding of IgG and (c) the binding of HRP-labeled anti-rabbit IgG were examined when the concentrations of the three reagents were, respectively, 1800 ng/ml, 86 ng/ml, and 344 ng/ml. The signal current reached its plateau after 15 minutes of incubation in the activation step. When the incubation time was halved to 7.5 minutes, 75 % of the current was retained. In the rabbit IgG exposure step, the current plateau was reached in 15 minutes, and shortening of the incubation period to 10 minutes resulted in only a 10% reduction in current. For the final step of binding HRP labeled anti-IgG, the current did not level off in 30 minutes, but increased linearly with time, becoming easily measurable in about 5 minutes.

These data demonstrated a separationless electrochemical immunoassay system, requiring no washing steps, nor toxic or unstable additives to the analyzed fluid. The platform of the assay is a redox hydrogel that conducts electrons, in which avidin and choline oxidase are co-immobilized. This hydrogel is permeable to large biological molecules, including antibodies and enzyme labeled antibodies. The choline oxidase in the gel catalyzes the reaction of choline and oxygen, whereby betaine aldehyde and hydrogen peroxide are produced within the sensing layer. Hydrogen peroxide is electroreduced in this layer to water at potentials negative of 400 mV (SCE) preferably between −70 mV (SCE) +150 mV (SCE), after components of the electrocatalyst are assembled in the sandwich of the immunoassay. Once the platform of co-immobilized avidin and choline oxidase in the electron conducting hydrogel is in place, the probe is activated with the desired biotinylated immunoreagent. If the assayed fluid contains the complementary immunoreagent and if a peroxidase-tagged probe of the immunoreagent is added, a cathodic current flows as a result of the catalyzed electroreduction of the $H_2O_2$. The detection limit of the assay is about 4 ng/ml for the IgG/anti-IgG system, and the assay of a sample is completed within about 20 minutes or less.

The magnitude of the observed current densities, 2 $\mu A/cm^2$, was high enough to provide for miniaturization to 10 micrometer diameter electrodes, sufficient to assure that mass transport and electron transport both be radial. Because in microelectrodes, where electron transport between the "wired" enzyme and the electrode is radial, the current density is higher by a factor of $4\pi$ than in the semi-infinite planar electrodes of the Example, it is estimated that the current will be of about 20 picoamperes in the 10 micrometer diameter electrodes.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

We claim:

1. An assay system for detecting a second member of a ligand—ligand receptor pair, the system comprising:
   a) an electrode coated with a film comprising a redox polymer;
   b) a first member of a ligand—ligand receptor pair that binds the second member, wherein the first member is immobilized in the redox polymer; and
   c) a third member that binds the second member, the third member being labeled with a detection marker;
   wherein binding of the second member to the first member and of the third member to the second member results in increased rate of oxidation or reduction of a detection compound, when a potential is applied to the electrode.

2. The assay system of claim 1, wherein the film further comprises an enzyme immobilized in the film, the enzyme generating the detection compound.

3. The assay system of claim 2, wherein the enzyme comprises one or more reaction centers, and wherein the reaction centers do not exchange electrons with the redox polymer.

4. The assay system of claim 1, wherein the film coating the electrode further comprises a binding agent.

5. The assay system of claim 4, wherein the binding agent is avidin or streptavidin.

6. The assay system of claim 4, wherein the binding agent comprises biotin or an analog thereof.

7. The assay system of claim 1, wherein the detection compound is hydrogen peroxide.

8. The assay system of claim 1, wherein the potential applied to the electrode is not more reducing than about −0.1 V versus a saturated calomel electrode (SCE) and not more oxidizing than about +0.3 V versus the saturated calomel electrode (SCE).

9. The assay system of claim 8, wherein the potential is not more reducing than −0.0V versus the saturated calomel electrode (SCE) and not more oxidizing than +0.4V versus the saturated calomel electrode (SCE).

10. The assay system of claim 3, wherein the one or more reaction centers of the enzyme are not electroreduced or electrooxidized at the potential applied to the electrode.

11. The assay system of claim 2, wherein the enzyme is choline oxidase.

12. The assay system of claim 1, wherein the detection marker is a peroxidase.

13. The assay system of claim 12, wherein the peroxidase is horseradish peroxidase or soybean peroxidase.

14. The assay system of claim 1, wherein the signal to noise ratio is at least 10.

15. The assay system of claim 1, wherein the detection compound is not generated via reaction by one or more of the first, second, or third members.

16. An assay system for detecting a second member of a ligand—ligand receptor pair, the system comprising:
   a) an electrode coated with a film comprising a redox polymer;
   b) a first member of a ligand—ligand receptor pair that binds the second member, wherein the first member is immobilized in the redox polymer;
   c) a third member that binds the second member, the third member being labeled with a detection marker; and
   d) a substrate-generating unit located within the redox polymer to generate a substrate of the detection marker,
   wherein binding of the second member to the first member and of the third member to the second member results in increased rate of oxidation or reduction of the detection compound, when a potential is applied to the electrode.

17. An assay system comprising:
   a) an electrode coated with a film comprising a redox polymer;
   b) a first member of a ligand—ligand receptor pair immobilized in the redox polymer;
   c) a second member of the ligand—ligand receptor pair that binds the first member;
   d) a third member that binds the second member, the third member being labeled with a detection marker; and
   e) a detection compound generated by electrooxidation or electroreduction within the film, wherein the detection compound comprises a substrate of the detection marker,
   wherein binding of the second member to the first member and of the third member to the second member results in increased rate of oxidation or reduction of the detection compound, when a potential is applied to the electrode.

* * * * *